(12) United States Patent
Jeong et al.

(10) Patent No.: US 6,451,348 B1
(45) Date of Patent: Sep. 17, 2002

(54) METHOD OF MANUFACTURING POROUS MATRIX-TYPE CONTROLLED RELEASE SYSTEMS USING EMULSION TECHNIQUE

(75) Inventors: Seo Young Jeong, Kyungki-do; Kuiwon Choi, Seoul; Ick-Chan Kwon, Seoul; Yong-Hee Kim, Seoul; Jae Bong Choi, Seoul; Kyu Back Lee, Seoul, all of (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/331,991

(22) PCT Filed: Dec. 31, 1997

(86) PCT No.: PCT/KR97/00289

§ 371 (c)(1),
(2), (4) Date: Jan. 3, 2000

(87) PCT Pub. No.: WO98/29100

PCT Pub. Date: Jul. 9, 1998

(30) Foreign Application Priority Data

Dec. 31, 1997 (KR) ............................................. 96-82443

(51) Int. Cl.⁷ .......................... A61K 9/00; A61K 47/00; C08J 9/00
(52) U.S. Cl. ........................ 424/486; 424/484; 514/772; 514/772.1; 514/772.2; 514/772.3; 514/953; 514/964; 514/975; 521/50; 521/61; 521/64; 521/65; 521/82; 521/88; 521/90; 521/97; 521/99; 521/106; 521/117; 521/130; 521/141; 521/149

(58) Field of Search ................................. 424/486, 484; 514/772.1, 772.2, 772.3, 953, 772, 964, 975; 521/50, 61, 64, 65, 82, 88, 90, 97, 99, 106, 117, 130, 141, 149

(56) References Cited

U.S. PATENT DOCUMENTS

| | | | |
|---|---|---|---|
| 4,305,502 A | 12/1981 | Gregory et al. | 206/532 |
| 4,371,516 A | 2/1983 | Gregory et al. | 424/485 |
| 4,616,047 A | 10/1986 | Lafon | 523/105 |
| 4,818,542 A | 4/1989 | DeLuca et al. | 424/491 |
| 5,626,861 A * | 5/1997 | Laurencin et al. | 424/426 |
| 5,723,508 A * | 3/1998 | Healy et al. | 521/61 |
| 5,942,253 A * | 8/1999 | Gombotz et al. | 424/501 |

OTHER PUBLICATIONS

Abstract of German Patent DE 2423811 A (1974).

* cited by examiner

*Primary Examiner*—Jose' G. Dees
*Assistant Examiner*—Frank Choi
(74) *Attorney, Agent, or Firm*—Scully, Scott, Murphy & Presser

(57) ABSTRACT

A method of manufacturing a porous matrix-type drug delivery system is provided. It comprises the steps of: dispersing, stirring, and emulsifying an aqueous solution of a drug in an organic solvent having a polymer compound and a surface active agent solved therein; thereafter forming it into a desirable matrix shape; lyophilizing or drying it at a low temperature or room temperature until the matrix surface is hardened; and drying it again in order to remove the water and the organic solvent.

6 Claims, 4 Drawing Sheets

METHOD OF MANUFACTURING POROUS MATRIX-TYPE CONTROLLED RELEASE SYSTEMS USING EMULSION TECHNIQUE

This application is a 371 of PCT/KR97/00289, filed on Dec. 31, 1997.

TECHNICAL FIELD

The present invention relates to a new method of preparing a matrix-type drug delivery system that allows a controlled-release of drugs, and which has various porosity. The system is manufactured by evaporating solvents from the matrix that is-formed from an emulsion-solution. The emulsion is made by emulsifying an aqueous solution containing a water-soluble drug in a polymer-dissolved organic solution using a surface-active agent.

BACKGROUND ART

Emulsion is a stable dispersion of one liquid in a second immiscible liquid, and typically, a surface-active agent is used in order to maintain the emulsion state.

The controlled-release is a characteristic that is capable of improving effects of medical usage, and of reducing its side-effects by making the drugs to be released from the drug-containing substance according to a time schedule. Matrix system means that the drug is evenly or unevenly dissolved or dispersed inside a matrix, in which the matrix substance is continuously aligned.

The release of a water-soluble drug from a non-biodegradable matrix, or from a biodegradable matrix having a low degradation rate typically follows first-order release kinetics, and its release rate decreases gradually as time passes. [Higuchi T., J. Pharm. Sci. 50, 874~875 (1961), Higuchi T., Pharm. Sci, 52, 1145~1149 (1063), Manduit et al, J. controlled Release. 25, 43~49 (1993)]. In general, the water-soluble drug cannot pass through the hydrophobic matrix. When a water-soluble drug is loaded in a hydrophobic polymer matrix below a percolation threshold, only the drug exposed on its surface is released at an initial period, while most of the drug still remains in the matrix even after a long time has passed. When the water-soluble drug is loaded above the percolation threshold, its release rate depends on the solubility of the drug in the body fluids, and on the diffusion of the drug through the water channels generated by the drug dissolution after the drug is in contact with body fluids. Therefore, in the system loaded with a low molecular compound having a high solubility, a large quantity of initial burst and fast release of the drug are shown. [Siegel et al, J. Controlled Release, 8,223~236 (1989), Saltzman et al, J. Biophys., 55, 163~171 (1989)].

In the case of a system in which a water-soluble drug of high osmotic activity is dispersed inside the water-insoluble polymer matrix, the water-soluble drug exposed on the surface is rapidly dissolved so as to form water-channels and is released at the initial period. The portion of the drug away from the water-channels functions as an osmotic pressure-causing material across the wall of the polymer matrix which functions as pseudo-semipermeable membrane. The osmotic pressure gradually breaks the polymer matrix from an outermost to an inside, and the drug is released in a controlled fashion. [Amsden et al, J.Controlled Release. 30, 45~56 (1994), Amsden B G and Cheng Y., J. Controlled Release, 31,21~32 (1994)]. Therefore, a drug that causes a high osmotic pressure can be released in a controlled-release fashion, and the remaining drug can be released even if in a case that the drug is loaded below the percolation threshold.

However, when the polymer matrix surrounding the drug is too thick, the possibility of breaking the polymer matrix wall is very low, and the rate of water passing through the polymer down to the drug is decreased, so that the release of the drug is very poor, and the more drug remains in the matrix. [Zhang et al, J.Pharm, Pharmacol. 46, 718~724 (1994), Amsden B G and Cheng Y., J. Controlled Release, 31, 21~32 (1994)].

To load a water-soluble drug on a hydrophobic matrix, either simple dispersion of drug particles in an organic polymer solution, or extrusion or compression of the drug-polymer mixture in a solid phase is used. Those loading methods do not allow the even distribution of the drug inside the matrix so that the rate change of the drug release is uneven as time passes.

DISCLOSURE OF THE INVENTION

A method of-manufacturing a porous matrix-type drug delivery system according to the present invention comprises the steps of: dispersing, stirring, and emulsifying an aqueous solution containing a water-soluble drug in an organic solvent in which a polymer compound and a surface active agent are dissolved therein; thereafter forming the resultant into a desirable matrix shape lyophilizing or drying at a low temperature or at a room temperature until the matrix surface is hardened; and drying again to remove water and organic solvents.

The porous matrix-type controlled-release system of the present invention is a matrix substance for oral or non-oral administration of drugs, and can be widely and efficiently used as medical treatment agents because the drugs can be released at a constant rate in a determined period.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

Figure 1:
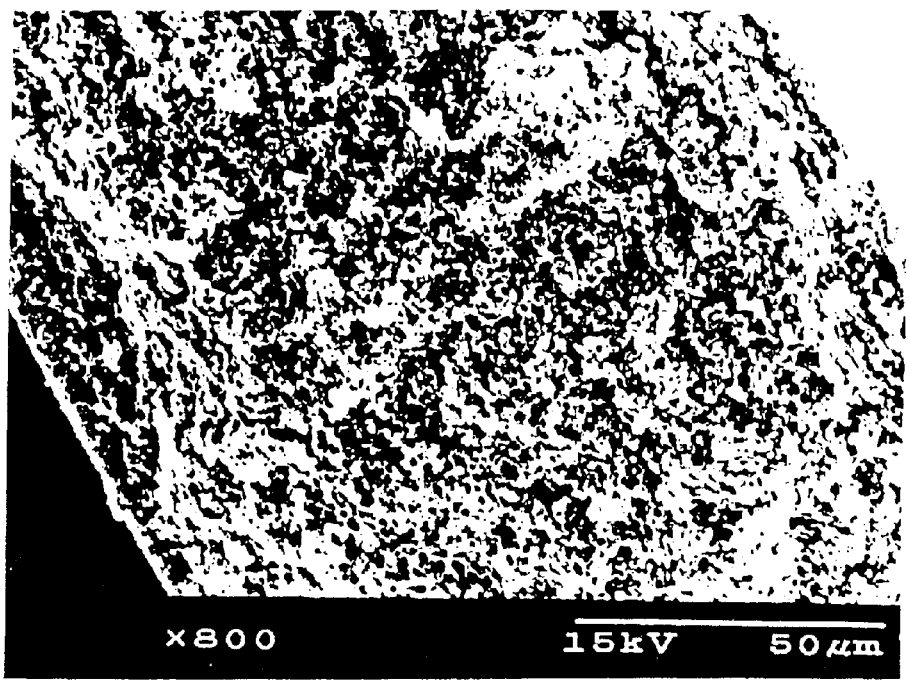
FIG. 1 shows a SEM (Scanning Electron Microscope) image of a cross-sectional view of a poly-L-lactide film containing 20 wt % of gentamycin according to a porous matrix-type controlled-release system of the present invention before release.

MODES FOR CARRYING OUT THE
PREFERRED EMBODIMENTS

The present invention is directed to provide a method of dispersing a water-soluble drug evenly into a hydrophobic polymer matrix by an emulsion method by using an oil-soluble surface active agent. The present invention is also directed to provide a method of manufacturing porous matrix-type controlled-release system containing an osmotically active, water-soluble drug which is released by an induced osmotic pressure across a pseudo-semipermeable polymer matrix and/or a surface active substance. The present invention has the following outstanding advantages:

1. Constant release rate of drug;
2. Controllable release rate of drug; and,
3. Very low residual drug.

Due to a high porosity, most of the drug contained therein is released and a low osmotic pressure is needed to break the matrix wall surrounding the drug.

To achieve the above objective and in accordance with the purposes of the present invention as embodied and described, a method of manufacturing a porous matrix-type drug delivery system is provided. The system is constructed in such a manner that an aqueous solution containing a water-soluble drug is dispersed and stirred to be emulsified in an organic solution that contains a polymer compound and a surface active agent. After forming it to a desired matrix shape, the emulsion is lyophilized immediately or dried at room temperatures (16 to 30° C.) for a predetermined time (which can vary depending on the boiling point of the organic solution used) until the surface of the matrix is hardened. After the drying, vacuum-drying (below 0.75 mmHg) is performed to remove organic solvents and water.

The polymer compounds which can be used as the matrix of the present invention are polylactide, lactide-glycolide copolymer, silicone rubber, ethylene-vinyl acetate copolymer, polyortho-ester copolymer, etc. Especially polylactide, lactide-glycolide polymer is suitable because it is widely used as biocompatible and biodegradable materials, as in the case of raw materials for suture materials. The polylactide used in this invention is a homopolymer having an average molecular weight of 100,000 (Polyscience. Inc of U.S., example 1,2,3), and the lactide-glycolide copolymer is Resomer RG858 (Boehringer Ingelheim of Germany, example 4). Ethylene-vinylacetate copolymer (Aldrich Chemical Company, Inc. of U.S. its vinyl-acetate is 33%, example 5), which does not decompose but its biocompatibility is excellent, is used.

The surface-active agent of the present invention can be selected from a group consisting of fat-acid, olefin, alkylcarbonyl, silicon elastomer, sulfate ester, petty alcohol sulfate, sulfate pete and oil, sulfonic acid-base, fat sulfonate, alkylaryl sulfonate, ligmin sulfonate, phosphoric acid ester, polyoxyethylene, polyoxyethylene caster oil, polyglycerol, polyol, imidazol, altanolamine, hetamine, sulfobecamine, phosphotide, polyoxyethylene-sorbitan fat acid ester (Tween), sorbitan ester (Span), etc. and preferably, sorbitan monooleate (Span 80) of a sorbitan ester. Its concentration is preferable to be 0.1 to 5 wt % for the emulsion solution. The release rate of the drug, that is, drug release amount per time is changed depending on the kind and density of the surface active agent (example 2). The usage of the surface active agent is limited to above, wherein the emulsion is difficult to achieve below those density, and above those density, the release rate is too slow, and side-effects may occur in clinical applications.

A variety of drugs can be used in the present invention. These include analgesics, anti-inflammatory agents, vermicide, cardiovascular drugs, urological drugs, antibiotic agents, anticoagulating agents, antidepressant, diabetes treatment agents, antiepileptic agents, antihypertensive agents, antifebrile, hormones, antiasthmatic agents, bronchodilators, diuretics, digestive agents, sedatives, hypnotics, anesthetics, nutritional and tonic agents, antiseptic agents, preservation agents, stabilization agents, insecticide, disinfectant, muscle-relaxant, antituberculosis and antileprosy agents, vaccines, etc. Although it depends on the therapeutic concentration of the drug, water-soluble drugs where the solubility of which is over 1 mg/ml is preferable. When the solubility is low, the maximum drug loading achievable by the present invention is too small.

As the organic solvents of the present invention, butyl alcohol, chloroform, cyclohexan, dichlorometan, dichloroethan, ethylacetate, ethylether, dipropylether, toluene, etc. can be used.

The volume ratio of the aqueous solution and the organic solvent is preferable to be 1:2~1:40. The initial burst of the drug can be increased by increasing the volume ratio of the aqueous solution. The reason why the range of the volume ratio is set is that the high volume ratio of the solutions makes the emulsion formation difficult, and even when the emulsion is formed, the initial release amount of drug is too high. The shape of the matrix can be manufactured variously depending on the purpose, such as film, surface coating, pellet, tablet, plate, rod, etc.

The emulsification can be achieved by using well-known tools such as stirrer, vortex mixer, homogenizer, ultrasonic device, microfluidizer, etc.

Reference will now be made in detail to the preferred embodiments of the present invention, but the substitutions and alterations can be made hereto without departing from the spirit and scope of the invention as defined by the claims.

EXAMPLE 1

Figure 2:
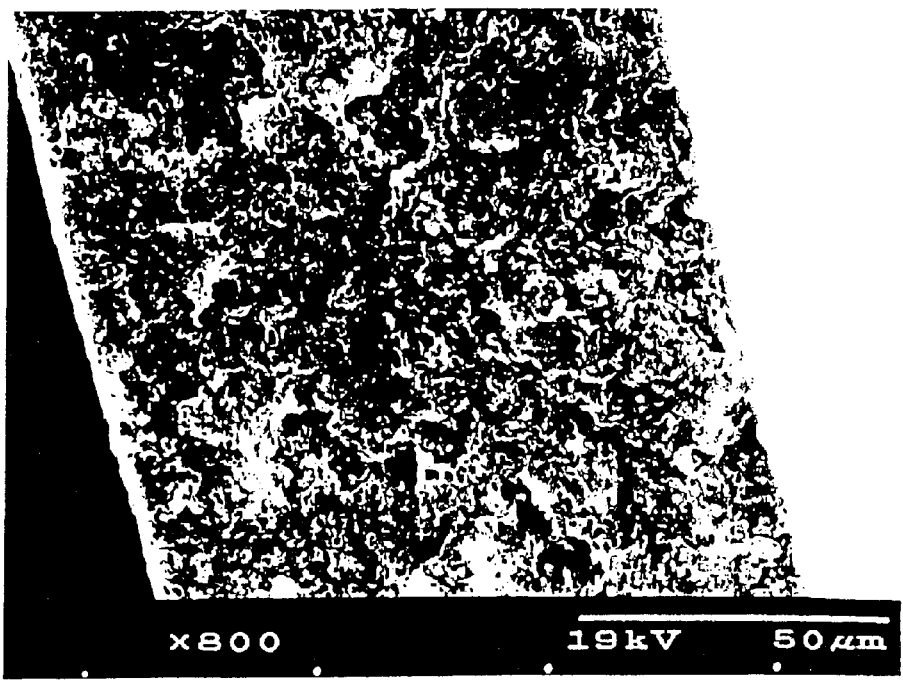
FIG. 2 shows a SEM image of a sectional view of a poly-L-lactide film containing 20 wt % of gentamycin according to porous matrix-type controlled-release system of the present invention after release.

A 50% aqueous gentamycin solution was poured into a polymer solution of dichloromethan having 16% of poly-L-lactide (weight averaged molecular weight of 100,000), and 3% of span 80 (wt %). The weight of gentamycin was 20% of the weight of poly-L-lactide. The mixture solution was evenly emulsified by using a vortex mixer, a stirrer and a sonicator. The emulsion was cast on a clean glass plate and the thickness was adjusted by using an applicator of 1 mm height. It was dried at room temperatures for 4 hrs. and then vacuum-dried for 24 hrs. to form a solid film. SEM pictures of the film were taken before and after the release of the drug. The porosity of the film was determined by the amount of water included in the emulsion. (FIG. 1 and 2).

Drug Release Embodiment

Except for the change of gentamycin concentration of the aqueous solution in example 1 to 25%, 35%, 50%, the films were manufactured in the same manner as example 1. The films were cut into same sizes, and the release rate was measured by immersing the films in PBS of pH 7.4.

Comparative Example 1

Initial Release

Figure 3:
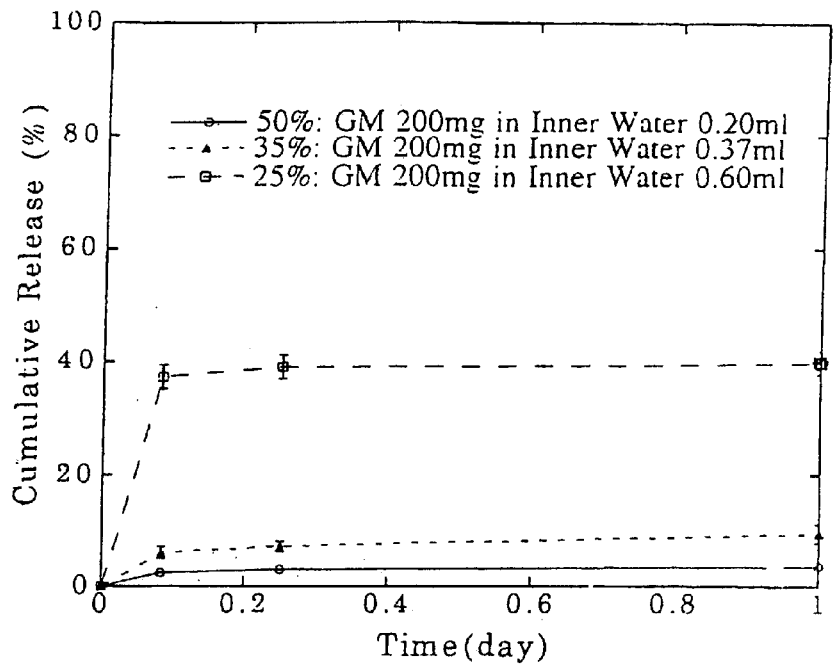
FIG. 3 is a graph showing an early release vs. time relation of a porous matrix-type controlled-release system according to the present invention.

The initial release of drug was increased with the increase of the water amount in the emulsion. (FIG. 3)

Comparative Example 2

O-Order Release for Long Term

Figure 4:
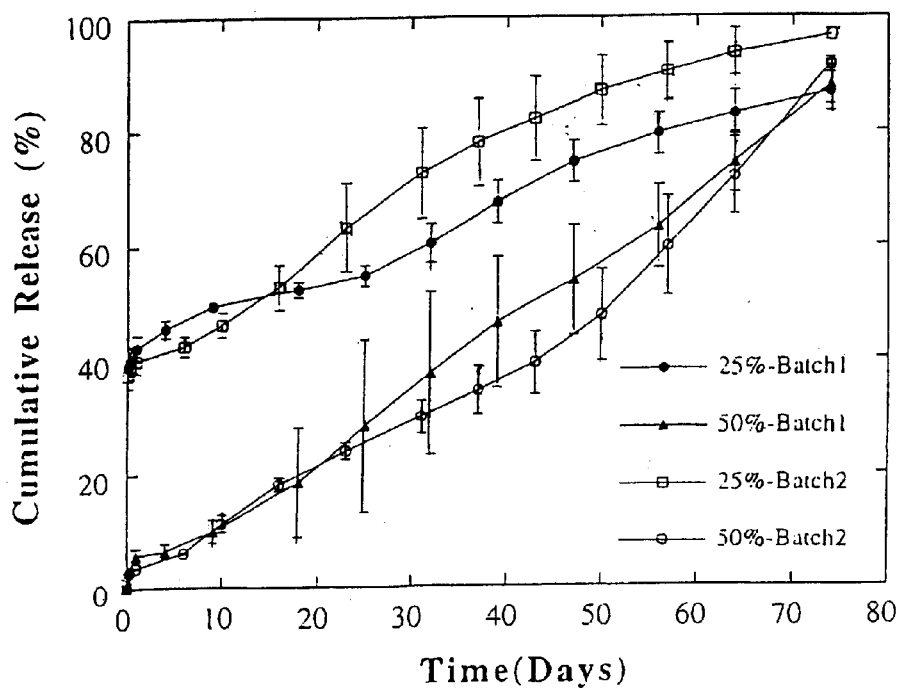
FIG. 4 is a zero-order release graph of the long term release vs. time relation of a porous matrix-type controlled-release system according to the present invention.

After the period of initial release, zero-order release is maintained for a long-time. (FIG. 4)

EXAMPLE 2

Figure 5:
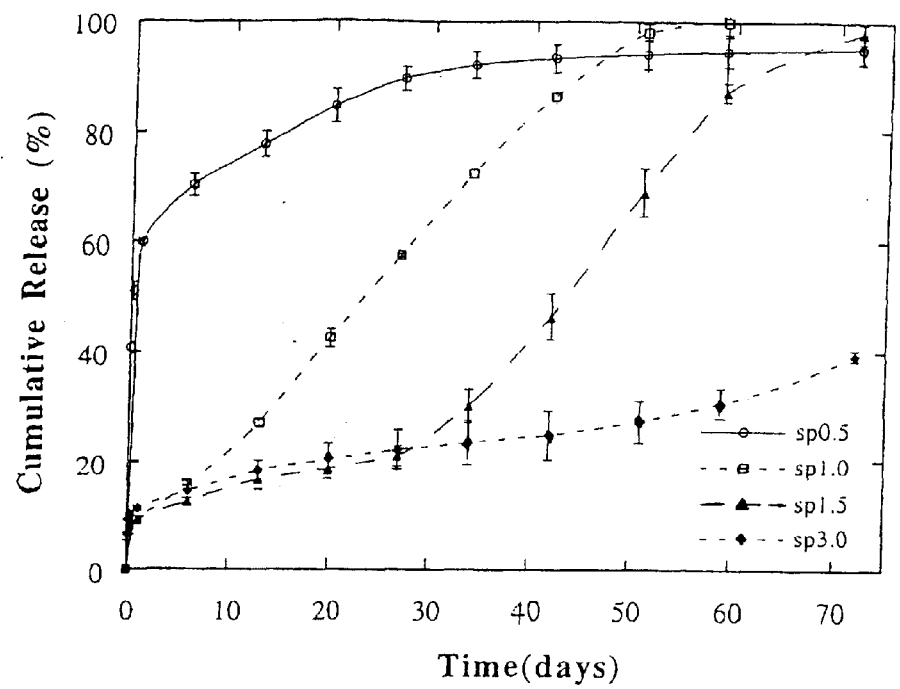
FIG. 5 is a release graph of a porous matrix-type controlled-release system of the present invention according to a change in the concentration of span 80.

Except for the change of gentamycin concentration of the aqueous solution in example 1 into 35%, and the change of span 80 concentration into 0.5%, 1%, 1.5%, 3%, the films were manufactured in the same way as example 1. The films were cut into same sizes and the drug was released in PBS of pH 7.4. The initial burst and release rate of the drugs were changed depending on the concentration of the span 80. (FIG. 5)

EXAMPLE 3

Figure 6:
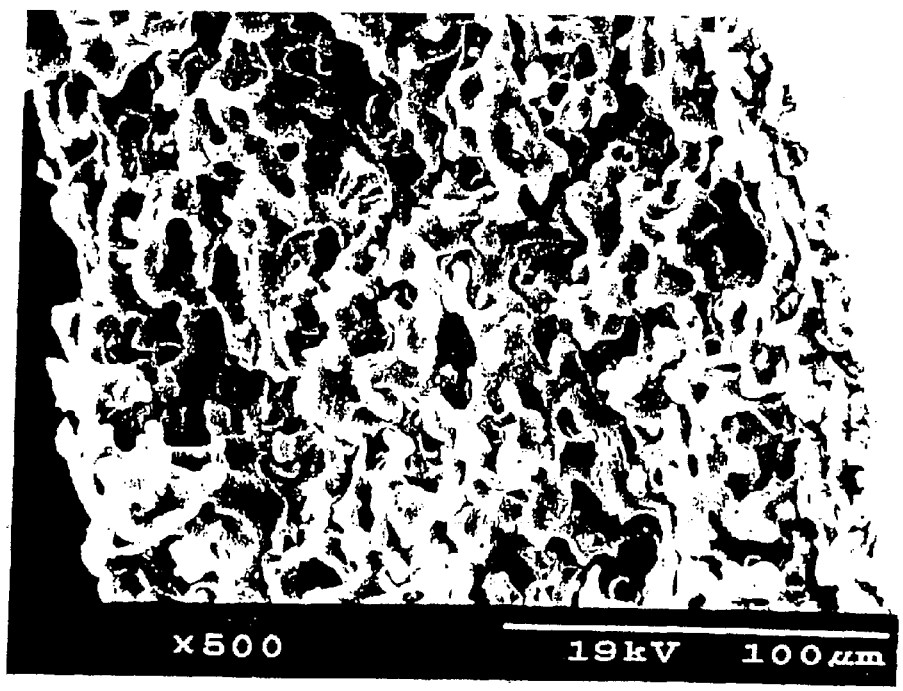
FIG. 6 shows a SEM image of a cross-sectional view of a poly-L-lactide film containing 10 wt % of cefotaxime sodium according to a porous matrix-type controlled-release system of the present invention.

A 10% aqueous cefotaxime sodium solution was poured into a polymer solution of methylene chloride having 16 wt % of poly-L-lactide (average molecular weight of 100,000), and 1 wt % of span 80. The weight of the cefotaxime sodium was 20 wt % of the weight of lactide-glycolide copolymer. The mixture solution was evenly emulsified by using a vortex mixer, a stirrer and a sonicator. The emulsion was cast on a clean glass plate and the thickness was adjusted by using an applicator of 1 mm height. It was dried at room temperatures for 4 hrs. and then was vacuum-dried for 24 hrs. to form a solid film. SEM pictures of the film were taken before and after the release of the drug. The porosity of the film was determined by the amount of water included in the emulsion. (FIG. 6)

EXAMPLE 4

Figure 7:
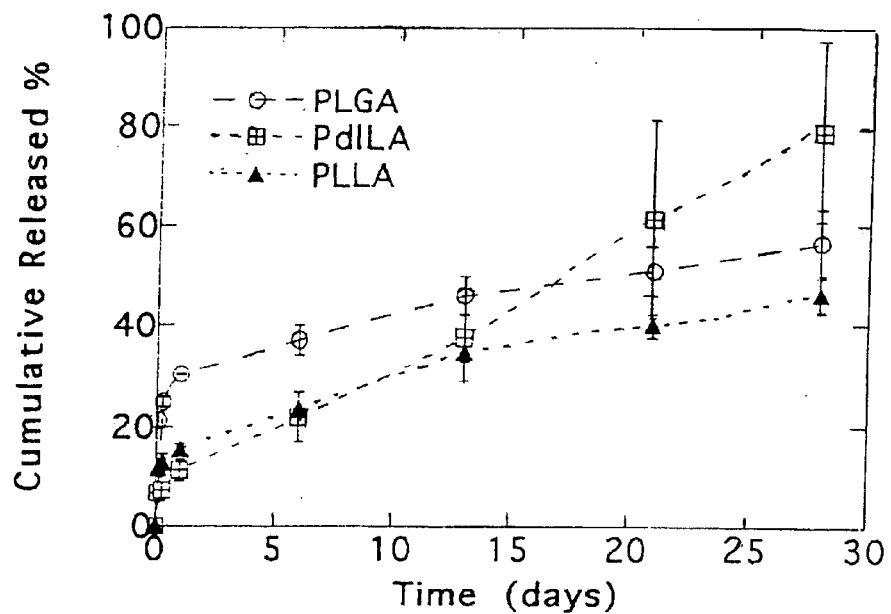
FIG. 7 is a drug release graph of polylactide-co-glycolide film and poly-D,L-lactide film containing 20 wt % of gentamycin sulphate according to a porous matrix-type controlled-release system of the present invention.

A 35 wt % aqueous gentamycin sulfate solution was put into a polymer solution of chloroform having 16 wt % of lactide-glycolide copolymer (Resomer RG858, Boehringer Ingelheim, Germany) and 1 wt % of span 80 or into a polymer solution of chloroform having 16 wt % of poly-D, L-lactid (Resomer R207, Boehringer Ingelheim, Germany), and 1 wt % of span 80. The weight of gentamycin sulfate was 20% of the weight of polymers. The mixture solution was evenly emulsified by using a vortex mixer, a stirrer and a sonicator. The emulsion was cast on a clean glass plate and the thickness was adjusted by using an applicator of 1 mm height. It was dried at room temperatures for 4 hrs. and then was vacuum-dried for 24 hrs. to form a solid film. The films were cut into same sizes and the drug was released in PBS of pH 7.4. The drug was also released in a controlled fashion even when using the lactide-glycolide copolymer or poly-D,L-lactide. Especially, the release rate of poly-D,L-lactide film was faster than that of poly-L-lactide film. (FIG. 7)

EXAMPLE 5

Figure 8:
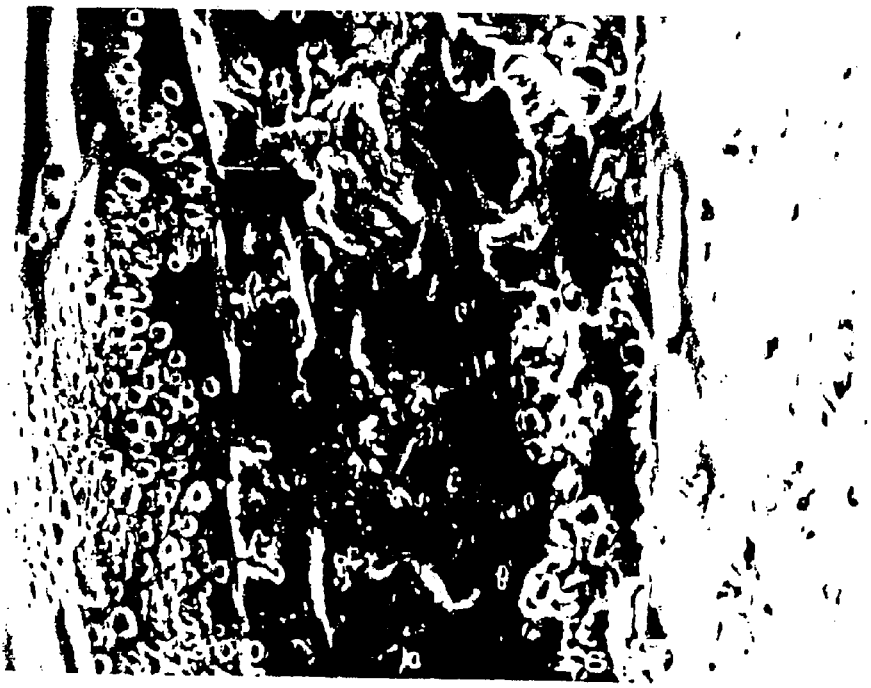
FIG. 8 shows a cross-sectional SEM view of a ethylene-vinylacetate copolymer film containing 20 wt % of gentamycin sulphate according to a porous matrix-type controlled-release system of the present invention.

A 35 wt % aqueous gentamycin sulfate solution was put into a polymer solution of chloroform having 20 wt % of ethylene-vinylacetate copolymer (weight averaged molecular amount 130,000, ethylene: vinylacetate=67:33), and 1 wt % of span 80. The weight of gentamycin sulfate was 20% of the weight of ethylene vinylacetate copolymer, The mixture solution was evenly emulsified by using a vortex mixer, a stirrer and a sonicator. The emulsion was cast on a clean glass plate and the thickness was adjusted by using an applicator of 1 mm height. It was dried at room temperatures for 4 hrs. and then vacuum-dried for 24 hrs. to form a solid film. SEM pictures of the film were taken before and after the release of the drug. The porosity of the film was determined by the amount of water included in the emulsion. (FIG. 8)

What is claimed is:

1. A method of manufacturing a porous matrix controlled release drug delivery substance wherein the drug is present in the pores of the matrix comprising the steps of:

dispersing, stirring, and emulsifying an aqueous solution containing a water soluble drug in an organic solvent in which a polymer compound and a surface active agent are dissolved in a water-in-oil type emulsion, wherein said surface active-agent is present in the amount of about 0.1 to about 5% wt of the emulsion;

thereafter forming the emulsion into a desirable matrix shape;

drying at room temperature until the matrix surface is hardened; and vacuum drying to remove water and the organic solvent.

2. The method as claimed in claim 1, wherein the polymer compound is selected from the group comprising of poly(l-lactide), poly(dl-lactide), polyglycolide, lactide-glycolide copolymers, poly ortho-ester copolymers, ethylene-vinyl acetate copolymers, and ethylene-vinyl alcohol copolymers.

3. The method as claimed in claim 1, wherein the surface-active agent is selected from the group consisting of sorbitan esters and polyoxyethylene sorbitans.

4. The method as claimed in claim 1, wherein the drug is a water-soluble drug for oral and non-oral administration that is dissolved in an inner aqueous solution inside the water-in-oil type emulsion.

5. The method as claimed in claim 1, wherein the organic solvent is selected from the group comprising of dichloromethane and chloroform.

6. The method as claimed in claim 1, wherein the volume ratio of the aqueous solution to the organic solvent is 1:2~1:40.

* * * * *

UNITED STATES PATENT AND TRADEMARK OFFICE
CERTIFICATE OF CORRECTION

PATENT NO.     : 6,451,348 B1
DATED          : September 17, 2002
INVENTOR(S)    : Seo Young Jeong et al.

It is certified that error appears in the above-identified patent and that said Letters Patent is hereby corrected as shown below:

<u>Title page,</u>
Item [30], "Dec. 31, 1997" should read -- Dec. 31, 1996 --

Signed and Sealed this

Thirteenth Day of May, 2003

JAMES E. ROGAN
*Director of the United States Patent and Trademark Office*